United States Patent [19]

Marrone et al.

[11] Patent Number: 5,208,332

[45] Date of Patent: May 4, 1993

[54] OPTICAL PROBE FOR THE CYTOCHROME P-450 CHOLESTEROL SIDE CHAIN CLEAVAGE ENZYME

[75] Inventors: Babetta L. Marrone; Daniel J. Simpson; Clifford J. Unkefer, all of Los Alamos; Thomas W. Whaley, Santa Fe, all of N. Mex.

[73] Assignee: The United States of America as represented by the United States Department of Energy, Washington, D.C.

[21] Appl. No.: 811,217

[22] Filed: Dec. 20, 1991

Related U.S. Application Data

[62] Division of Ser. No. 680,978, Apr. 5, 1991, Pat. No. 5,110,725.

[51] Int. Cl.$^5$ .......................................... C07D 265/38
[52] U.S. Cl. ................................. 544/102; 544/35; 544/37; 544/347; 546/102; 546/104; 549/223; 549/16
[58] Field of Search ................ 544/102, 35, 37, 347; 549/223, 16; 546/102, 104

[56] References Cited

U.S. PATENT DOCUMENTS 5,110,725 1/1992 Marrone et al. .................... 435/11

OTHER PUBLICATIONS

Simpson, Daniel, et al., *J. Org. Chem.*, 56(18), pp. 5391-5396, 1991.

Marrone, Babetta, et al., *Endocrinology*, 128(5), pp. 2654-2656, 1991.

*Primary Examiner*—Marianne M. Cintins
*Assistant Examiner*—Kimberly Kestler
*Attorney, Agent, or Firm*—Ray G. Wilson; Paul D. Gaetjens; William R. Moser

[57] ABSTRACT

An optical probe enables the study of enzyme activity by absorbance spectroscopy or by sensitive fluorescence methods. In particular, the probe provides the ability to monitor the activity of cytochrome P-450$_{scc}$ enzyme, the rate limiting enzyme for steroid biosynthesis. Located on the inner mitochondrial membrane, P-450$_{scc}$ catalyzes the conversion of cholesterol to pregnenolone and isocapraldehyde by sequential oxidations of the cholesterol side chain. The fluorogenic probe includes a cholesterol-like steroid linked to a chromophore through a linking group. The chromophore is selected to have little optical response when linked to the steroid substrate and an enhanced optical response when cleaved from the substrate and linking group. Thus, a fluorescent anion that can be optically detected is generated by the side-chain cleavage reaction during steroidogenesis.

2 Claims, 3 Drawing Sheets

Steroid
R = H, alkyl, or alkyl-CO-

Chromophore
$R_2$ = H, halogen, alkyl, -O-alkyl,
-COO alkyl, or -COOH

X = O, S, NH, or N-alkyl

Z = O or N, N-dialkyl

L = Linking group

, or n = 2 or 3

X' = O or S

OPTICAL PROBE FOR THE CYTOCHROME P-450 CHOLESTEROL SIDE CHAIN CLEAVAGE ENZYME

This is a division of application Ser. No. 07/680,978 filed Apr. 5, 1991 now U.S. Pat. No. 5,110,725.

BACKGROUND OF INVENTION

This invention relates to the study of enzymatic events in cells and, more particularly, to the study of enzymatic events in single cells by optical detection methods. This invention is the result of a contract with the Department of Energy (Contract No. W-7405-ENG-36).

Enzymatic events in cells include steroid biosynthesis. Identification of such events provides important information for ongoing research on factors regulating the growth and differentiated function of steroidogenic cells. In one particular event, the cytochrome P-450 cholesterol side-chain cleavage enzyme (P-450$_{scc}$) controls the rate-limiting step of steroidogenesis, the enzymatic conversion of cholesterol to pregnenolone.

In one attempt to characterize the side-chain cleavage event, the amount of P-450$_{scc}$ has been investigated by immunofluorescent staining of P-450$_{scc}$ with an antibody to the P-450$_{scc}$ enzyme. See N. B. Goldring et al., "Immunofluorescent Probing of the Mitochondrial Cholesterol Side-Chain Cleavage Cytochrome P-450 Expressed in Differentiating Granulosa Cells in Culture," 119 Endocrinology, pp. 2821–2832 (1986). This technique, however, can not measure P-450$_{scc}$ enzyme activity since the immunofluorescent staining requires cell fixation.

One measure of the cleavage event is the amount of the side chain fragment produced by the enzymatic cleavage. The enzymatic conversion of cholesterol to pregnenolone by the P-450$_{scc}$ enzyme can be measured from the amount of radioisotopically labeled isocapraldehyde formed from cholesterol when the sterol substrate bears a radioisotope on the side chain. See R. B. Hochberg et al., "A Simple and Precise Assay of the Enzymatic Conversion of Cholesterol in Pregnenolone," 13 Biochemistry, No. 13, pp. 603–608 (1974).

It would be desirable, however, to use a rapid, sensitive, single cell analysis technique, such as fluorescence detection in flow cytometry, for the study of these metabolic events. However, fluorescent probes have not been available that are specific to a particular cell function, such as the activity of a key enzyme. This problem is addressed by the present invention and a fluorescent probe is developed that is specific for identification of the rate-limiting cholesterol side-chain cleavage by the P-450$_{scc}$ enzyme.

Accordingly, it is an object of the present invention to provide a fluorescent probe to measure the activity of the enzyme responsible for the conversion of cholesterol to other steroids.

It is another object of the present invention to provide a steroid probe that is non-fluorescent until cleaved by P-450$_{scc}$.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the apparatus of this invention may comprise a probe for use in quantifying the activity of the P-450$_{scc}$ enzyme in steroidogenesis. The probe is a fluorogenic substrate for the P-450$_{scc}$ enzyme having a cholesterol-like steroid with the side chain at the C-22 position replaced with a chromophore selected from the xanthene dye group.

In another characterization of the present invention, a method for quantifying the activity of the P-450$_{scc}$ enzyme allows the rate-limiting process in steroidogenesis, the conversion of cholesterol to pregnenolone, to be examined. A fluorogenic probe is a cholesterol-like steroid with the side-chain at the C-22 position replaced with the chromophore resorufin ether. The side chain is cleaved from the probe by the P-450$_{scc}$ enzyme to generate the steroid pregnenolone and a highly fluorescent resorufin anion. The presence of the resorufin anion is thereafter detected by sensitive optical detection methods, such as absorbance spectroscopy or fluorescence detection used in flow and image cytometry, to measure P-450$_{scc}$ expression and regulation in cells or subcellular fractions or with a purified or semi-purified enzyme preparation.

In another characterization of the present invention, a process is provided for synthesizing a fluorescent substrate for use in quantifying activity of the P-450$_{scc}$ enzyme. The process includes the following steps: a. treating 3$\beta$-acetoxy-22,23-bisnor-5-cholenic acid with thionyl chloride to yield 3$\beta$-acetoxy-22,23-bisnor-5-cholenyl chloride; b. reducing said acid chloride with lithium tri-tert-butoxyaluminohydride to yield the alcohol 3$\beta$-acetoxy-5-cholene-22-ol; c. treating said alcohol with p-toluenesulfonyl chloride in pyridine to yield the tosylate 3$\beta$-acetoxy-22-p-toluenesulfonyl-5-cholenate; d. dissolving said tosylate in dimethyl sulfoxide and treating with an excess of resorufin sodium salt at temperatures between 55–70° C. to yield the product 3$\beta$-acetoxy-22-phenoxazonoxy-5-cholene; e. separating said product by chromatography and hydrolysis with KOH/methanol to yield said fluorogenic substrate 22-phenoxazonoxy-5-cholene-3$\beta$-ol; and f. separating said fluorogenic substrate by chromatography on silica.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

In accordance with the present invention, an optical probe enables the study of enzyme activity in single steroidogenic cells by absorbance spectroscopy or by sensitive fluorescence methods. In particular, the probe provides the ability to monitor in real time the activity of cytochrome P-450$_{scc}$ enzyme, the rate limiting enzyme for steroid biosynthesis. Located on the inner mitochondrial membrane, P-450$_{scc}$ catalyzes the conversion of cholesterol to pregnenolone and isocapraldehyde by sequential oxidations of the cholesterol side chain.

Figure 1A:
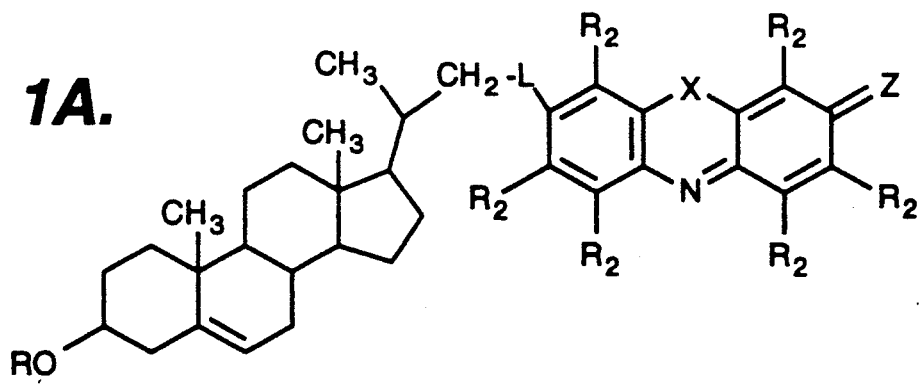
FIGS. 1A–C illustrate the chemical composition of optical probes according to the present invention.
Figure 1B:
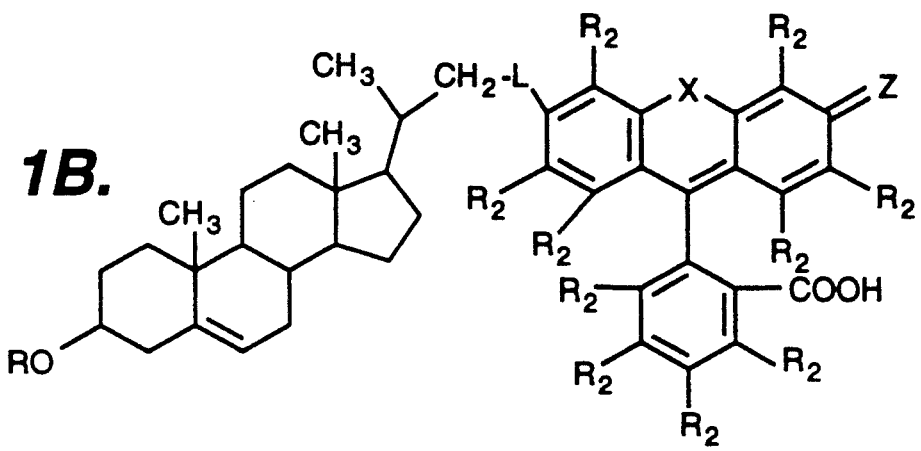
Figure 1C:
Figure 1C:
Figure 1C:
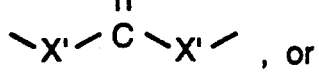
Figure 1C:
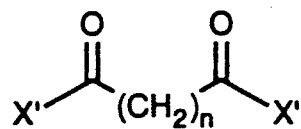

FIGS. 1A-C depict the chemical composition of the components of an optical probe according to the present invention. A cholesterol-like steroid is linked to a chromophore through a linking group. In order to bind to the enzyme, the steroid substrate, FIGS. 1A and 1B, has a 3β-hydroxy group, unsaturation in the 5-6 bond, and has cholesterol-like stereochemistry at the C-17 and C-20 αpositions. The R position can be filled from the group consisting of H, alkyl, and alkyl— CO—. As used herein, the term alkyl is limited to the low alkyl groups with 1-6 carbon atoms, i.e., methyl, ethyl, isopropyl, etc.

The chromophore is selected to have advantageous spectral properties, i.e., to have little optical response when linked to the steroid substrate and an enhanced optical response when cleaved from the substrate and linking group. The chromophore molecule should also be of modest size to not interfere with the side chain cleavage reaction. A preferred chromophore is selected from the xanthene dyes, linked as shown in FIG. 1A or 1B, where R$_2$ is H, halogen, alkyl, —O—alkyl, —COOalkyl, or —COOH; X is O, S, NH, or N-alkyl; and Z is O or N,N-dialkyl.

The structural requirements of the linking group, FIG. 1C, are not stringent, where the X' position can be filled from either O or S. Any one of the three linking groups may be selected, with a preferred link being the simple O or S link. The group containing an intermediate C provides a somewhat longer link and the group containing the (CH$_2$)$_n$ provides longer linker arms. All three linking groups are expected to be cleaved with the P-450$_{scc}$ enzyme and to not interfere with the generation of the active chromophore.

Figure 2:
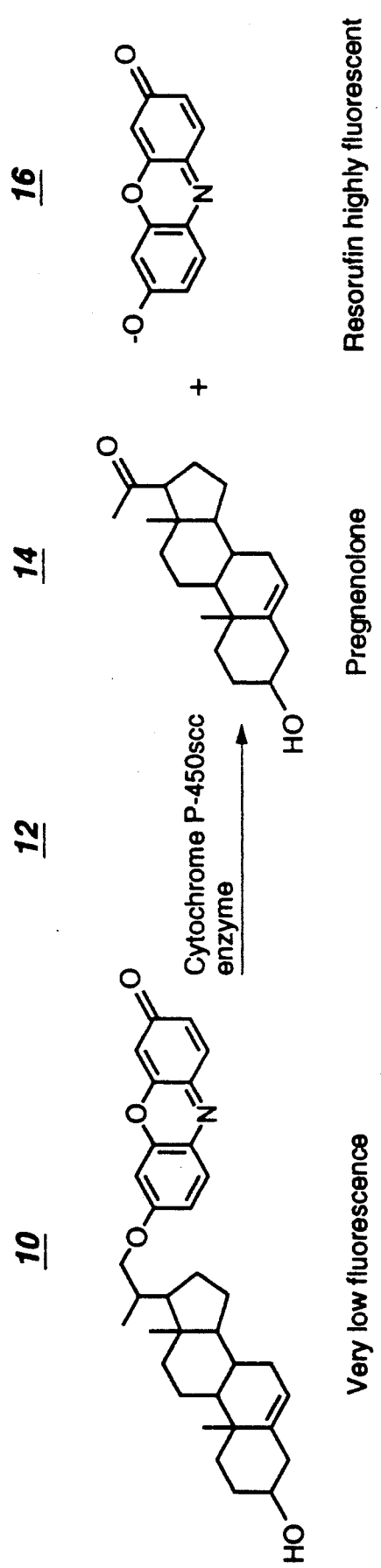
FIG. 2 illustrates the side-chain cleavage of a cholesterol-like steroid by the P-450$_{scc}$ enzyme.

Referring now to FIG. 2, the P-450$_{scc}$ probe 10 is a cholene-based steroid covalently conjugated at the C-22 position to resorufin. As a result of this conjugation the resorufin fluorescence is shifted and has a 40-fold lower quantum efficiency than the resorufin anion. Specificity of probe 10 for the P-450$_{scc}$ enzyme is achieved by incorporating known structural and stereochemical features to the cholene-ring for enzyme recognition. Generation of a fluorescent signal is obtained by release of the resorufin moiety 16 by the side chain cleavage enzyme.

The mechanics of P-450$_{scc}$ enzyme-substrate (probe 10) binding and side chain cleavage 12 are well known. Once a substrate 10, such as cholesterol, is recognized and positioned into the enzyme active site, side chain cleavage by P-450$_{scc}$ 12 proceeds in three oxidative steps: 1) hydroxylation of C-22 at the pro-R methylene position; 2) hydroxylation of the adjacent 20α-methine position to give a vicinal diol intermediate; and 3) oxidative cleavage of the diol to give pregnenolone and a side chain fragment 16. In order to bind to the enzyme, a steroid substrate should contain a 3β-hydroxy group, unsaturation in the 5-6 bond, and have cholesterol-like stereochemistry at the C-17 and C-20αpositions. The structural requirements of the side chain beyond the C-22 position are less stringent.

Resorufin (7-hydroxy-3H-phenoxazin-3-one) was chosen as a fluorogenic reporter because of its advantageous spectral properties and its modest size. Covalently conjugated through its oxy anion, resorufin shows a large increase in absorbance energy (approximately 110 nm), a drop in absorbance extinction (by approximately ½) relative to the anion, and a 40-fold difference in fluorescence quantum yield. Presumably, metabolism of a resorufin ether 10 by P-450$_{scc}$ proceeds by hydroxylation at the C-1 position of the ether side chain, to yield a resorufin hemiacetal that undergoes cleavage to afford the highly fluorescent resorufin anion. The fluorescence signal generated by the formation of resorufin anion is a quantitative indicator of enzyme activity.

Figure 3:
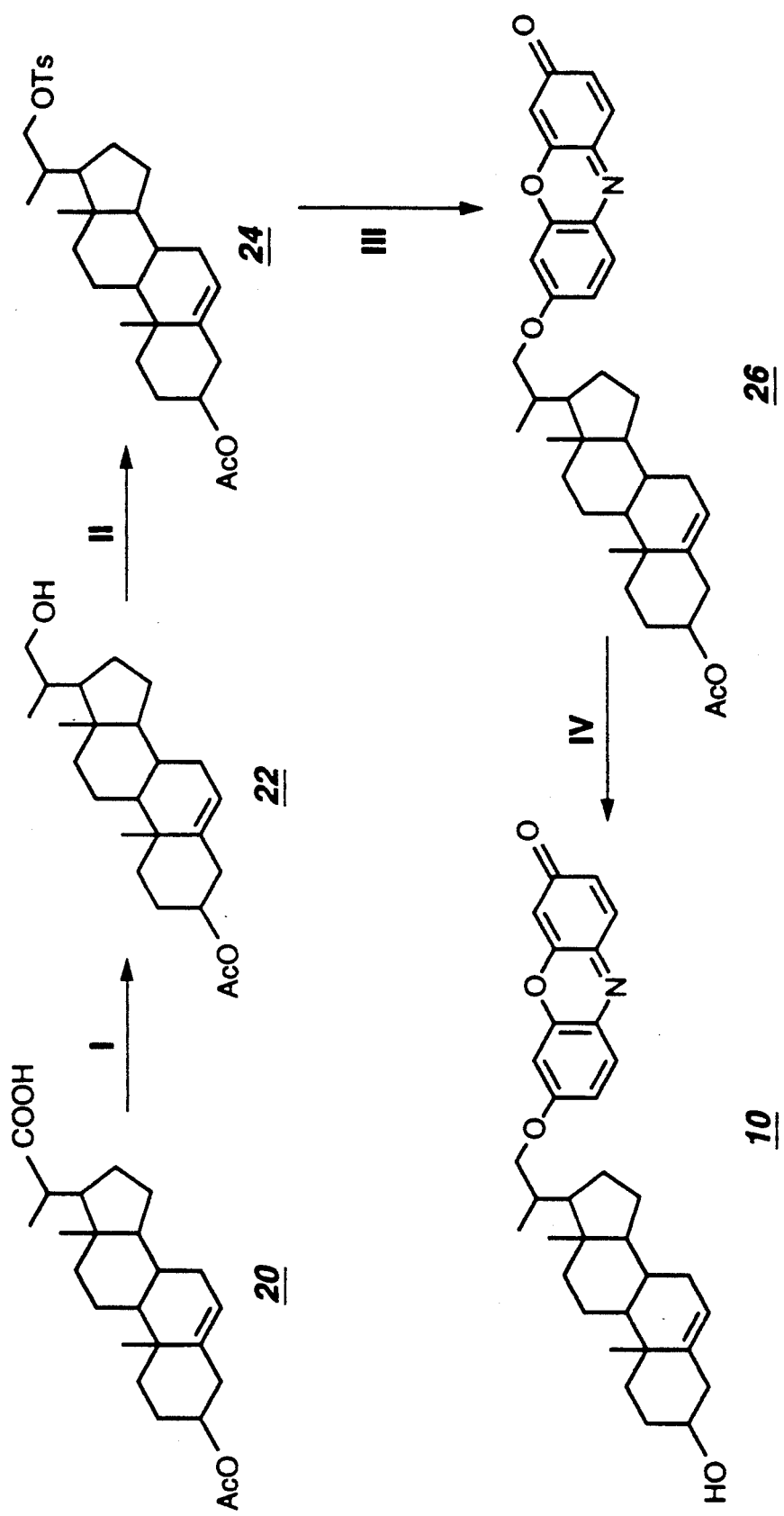
FIG. 3 illustrates the chemical reactions to generate a fluorescent probe according to one embodiment of the present invention.

Synthesis of fluorogenic substrate probe 10, 22-phenoxazonoxy-5-cholene-3β-ol, is shown in the scheme depicted in FIG. 3. In step I, 3β-acetoxy-22, 23-bisnor-5-cholenic acid 20 (1.0 g, Steraloids, Inc., Wilton, NH) was dissolved in methylene chloride (5 mL) and cooled to 0-5° C. with an ice bath. The selected R group was alkyl —CO—, and particularly tert-butoxy. Thionyl chloride (900 mg) was added dropwise via a syringe to the clear solution. The solution was stoppered, allowed to warm to room temperature, and stirred for 20 h. This mixture was diluted with methylene chloride, extracted with aqueous NaCl and dried and evaporated to a white solid.

This crude acid chloride was dissolved in methylene chloride (5 mL) and cooled to −65° C. (dry ice/acetone). Lithium tri-tert-butoxyaluminhydride in tetrahydrofuran (1.0 M, 2.3 mL) was added under argon to the acid chloride over 20 min. The reaction was kept at −65° C. for 1 h after addition, then allowed to warm to room temperature. Excess hydride reagent was destroyed by the slow dropwise addition of water. The mixture was extracted with methylene chloride. The organic layer was washed extensively with 1.0 N HCl, aqueous NaCl, and dried and evaporated. Compound 22, 3β-acetoxy-5-cholene-22-ol, was purified by column chromatography eluting with 1% methanol/methylene chloride and obtained as a solid (640 mg) from methylene chloride/n-hexane.

In step II, compound 22 was dissolved in dry pyridine (1 mL) in a small reacta-vial and p-toluenesulfonyl chloride (175 mg) was added. The vial was capped and stirred for 20 h. This mixture was diluted with ether, washed with 0.1 N HCl (3×50 mL), and dried and evaporated to a colorless oil. Compound 24 (185 mg), 3β-acetoxy-22-p-toluenesulfonyl-5-cholene, was recovered as a crystalline white solid from ether/n-hexane.

For step III, steroid 24(240 mg) was suspended in dimethyl sulfoxide (3 mL) and combined with resorufin (200 mg). This mixture was stirred under argon at 55° C. for 10 days. The dimethyl sulfoxide was removed by lyophylization (10 h, 10$^{-5}$ torr). The resulting solid was suspended in methylene chloride and filtered to remove unreacted resorufin and a bright orange material. Thin layer chromatography showed one orange spot, more polar than the tosylate precursor, as seen after development with phosphomolybdic acid. Compound 24 was purified by flash chromatography (eluting with 3% tetrahydrofuran/methylene chloride) and obtained as small orange needles from methylene chloride/n-hexane. This process yielded 22 mg of compound 26, with 140 mg of compound 24 remaining unreacted. The unreacted compound can be recycled through step III to produce additional compound 26.

The desired fluorogenic probe 10 was then generated in step IV. Acetate compound 26 was suspended in 5% KOH/methanol (2 mL), containing approximately 1% water, and refluxed for 30 min while argon was bubbled through the solution. After cooling, methylene chloride was added. This mixture was washed with 1 M HCl, water, and was dried and evaporated. Thin layer chromatography (TLC) showed two spots, one minor spot ($R_f = 0.5$) of compound 26 and the more polar product ($R_f = 0.2$) 10. Because of the small amount of material (yield of 7 mg), purification was achieved by preparative-scale TLC eluting with 3% methanol/methylene chloride and the product recovered was obtained as an orange solid from methylene chloride/n-hexane. It will be appreciated that the above protocol may generally be used to synthesize fluorogenic probes from starting materials appropriate to the chemical groups depicted in FIG. 1.

Fluorogenic probe 10 has been shown to be selective for P-450$_{scc}$ activity in intact mitochondria and cells. A saturated stock solution of probe 10 was made in 95% ethanol and filtered with a 0.2 μm filter to a concentration of 100μM. Probe 10 was added at 1:50 or 1:100 dilutions to cell or mitochondria suspensions.

Cell Preoarations: Granulosa cell layers were collected separately from the 5 largest preovulatory follicles of laying hens and cells were dispersed by collagenase digestion (Endocrinology 122:651–658). The cell concentration was adjusted to $1 \times 10^6$ cells/mL in modified medium 199 (no phenol red; added 25 mM HEPES, 0.35 g/L sodium bicarbonate, 100 mg/L 1-glutamate, and 1 g/L bovine serum albumin). The MA-10 cells (Endocrinology 108:88–95) were grown in RPMI-1640 medium supplemented with 15% horse serum and used three days after plating. Cell cultures of the Chinese hamster ovary (CHO) cell line were grown in spinner flasks with Ham's F-10 medium supplemented with 15% bovine calf serum. Media were obtained from Gibco BRL (Gaithersburg, MD) and sera were obtained from HyClone Laboratories (Logan, UT). Except where indicated all other reagents for cell preparations were obtained from Sigma Chemical Co. (St. Louis, MO). Cells in suspension ($1 \times 10^6$/mL) were kept on ice prior to use and at 37° C. during all incubations with probe 10.

Spectrofluoremetry: Fluorescence emission measurements were obtained on a SPEX Fluorolog-II spectrofluorometer (SPEX Industries, Inc., Edison, NJ) fitted with a thermostatted cuvette holder and interfaced to an IBM-AT computer for data collection and processing. Resorufin fluorescence was measured from 550–700 nm (8 nm slit width) with 530 nm excitation (10 nm slit width). Spectra were background-corrected by spectral subtraction of the initial (zero) time point. Samples were incubated at 37° C. during the experiment.

Flow Cytometry: For microspectrofluorometric demonstration the Fourier transform flow cytometer (FTCS-1) at Los Alamos National Laboratory (SPIE Proceedings, Bioimaging and Two-Dimensional Spectroscopy, 1205:126–133) was used to analyze spectral changes in the P-450$_{scc}$ probe fluorescence over time. A single argon laser tuned to 514 nm was used to excite both the substrate and product. The spectrum of the expected fluorescent product, resorufin, with an emission maximum of 588 nm, and the spectrum of the fluorogenic substrate, with an emission maximum of 562 nm were obtained from each sample.

The specificity of the probe for the P-450$_{scc}$ enzyme was demonstrated initially on a spectrofluorometer using mitochondrial preparations from chicken granulosa and MA-10 cells. Both time (30 min to 5 h) and substrate concentration-dependent (from 0.01 to 2 μM) resorufin production was observed with these steroidogenic mitochondria. The addition of known inhibitors of P-450$_{scc}$ enzymatic activity (aminoglutethimide and ketoconazole) attenuated the observed fluorescence. Mitochondrial preparations from nonsteroidogenic CHO cells showed no production of fluorescence.

To confirm cellular metabolism, both MA-10 and granulosa cell suspensions were incubated with varying concentrations of the probe substrate. Fluorescence emission was monitored at discrete times from 0–4 h. A linear increase in resorufin fluorescence was observed over time and was associated with the cellular metabolism of the probe by the P-450$_{scc}$ enzyme. Based on the amount of fluorescence in a typical cell incubation the cumulative conversion of the probe was in the concentration range of 100–300 pM. After long (3–5 h) incubations of granulosa or MA-10 cells with a high concentration (1–2 μM) of the P-450$_{scc}$ probe, a two-fold accumulation of progesterone over the background progesterone content of the cells was measured by specific progesterone radioimmunoassay (Endocrine Sciences, Tarzana, CA).

The Fourier transform flow cytometer was used to track the metabolism of the fluorogenic substrate in individual granulosa cells. The spectral information obtained on a cell-by-cell basis is used to resolve fluorochromes in the cells with highly overlapping emission spectra. Using this instrument, cellular fluorescence of the substrate is resolved from the cellular fluorescence of the product, resorufin anion, based on their unique spectral characteristics during the uptake and metabolism of the P-450$_{scc}$ probe.

By monitoring spectral changes in the cellular fluorescence at discrete time points from 30 min to 5 h with the FTCS-1 an increased metabolism of the substrate to the product resorufin was observed. The slope of the cell distribution shifted from one that was aligned primarily with the substrate to one that was aligned essentially 100% with the product resorufin after 5 h. A linear increase in the average ratio of the two fluorescent components (substrate and resorufin) was observed in the accumulation of resorufin fluorescence over time. By comparison, in experiments using nonsteroidogenic CHO cells, there was no evidence of significant metabolism of the substrate to resorufin. Following a 3 h incubation of the P-450$_{scc}$ substrate with CHO cells, cellular fluorescence remained primarily consistent with the substrate spectrum.

Conventional flow cytometric analysis of P-450$_{scc}$ activity was demonstrated in a two-laser experiment on a multiparameter flow cytometer in which green (substrate) fluorescence and red (resorufin) fluorescence were measured at discrete time intervals from 5 min to 2 h after allowing granulosa cells to react with the P-450$_{scc}$ probe at 37° C. Uptake of the substrate (green fluorescence) plateaued at 30 minutes, presumably as the cells equilibrated with the P-450$_{scc}$ probe in solution. By comparison, product (red florescence) continued to increase in cells during the incubation.

Thus, a mechanism-based, fluorogenic probe substrate for the P-450$_{scc}$ enzyme is shown to be a sensitive, quantitative indicator of P-450$_{scc}$ activity in populations of steroidogenic cells using fluorescence detection methods. Moreover, preliminary studies in granulosa cells have also shown that acute gonadotropin treatment increases resorufin fluorescence due to metabolism of the substrate, suggesting that the P-450$_{scc}$ probe can be used for the study of enzyme regulation. The P-450$_{scc}$ probe, because of its specificity and the sensitivity afforded by fluorescence detection, should have widespread applicability to the study of endocrine mechanisms regulating P-450$_{scc}$ enzyme activity during various stages of growth, differentiation, and disease in steroidogenic cell populations.

The foregoing description of an embodiment of the invention have been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An optical probe for use in quantifying the activity of the P-450$_{scc}$ enzyme, wherein the probe comprises Y-L-Q, where Y is a cholesterol-like steroid selected from the group consisting of

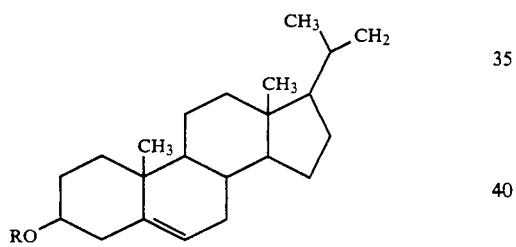

where R = H, alkyl, alkyl—CO—;

L is a linking group selected from the group consisting of

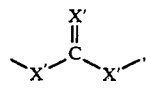
—X'—, where n = 2 or 3
X' = O or S; and

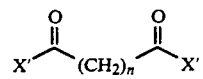

and

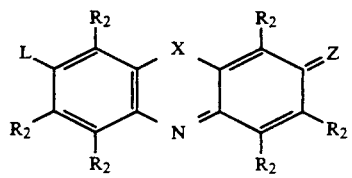

Q is a chormophore selected from the group consisting of

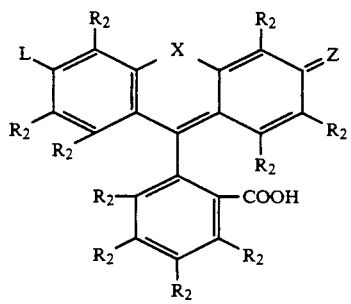

where R$_2$ = H, halogen, alkyl,
—O—alkyl, —COOalkyl,
or —COOH
X = O, S, NH, or N—alkyl
Z = O or N, N—dialkyl.

and

2. An optical probe according to claim 1, consisting essentially of the fluorogenic substrate 22-Phenoxazonoxy 5-cholene-3b-ol.

* * * * *